United States Patent [19]

Davis

[11] Patent Number: 5,720,949
[45] Date of Patent: Feb. 24, 1998

[54] FOAMABLE COSMETIC MASK PRODUCT

[75] Inventor: Jeffrey Davis, Aurora, Ohio

[73] Assignee: Bristol-Myers Squibb Company, New York, N.Y.

[21] Appl. No.: 643,814

[22] Filed: May 6, 1996

[51] Int. Cl.$^6$ .................................................. A61K 31/74
[52] U.S. Cl. ........................ 424/78.03; 424/400; 424/401
[58] Field of Search .................................. 424/400, 401, 424/78.03

[56] References Cited

U.S. PATENT DOCUMENTS

| | | | |
|---|---|---|---|
| 4,126,142 | 11/1978 | Saute | 132/7 |
| 4,272,544 | 6/1981 | Cella et al. | 424/273 |
| 4,592,855 | 6/1986 | Gioffre et al. | 252/89.1 |
| 4,767,618 | 8/1988 | Grollier et al. | 424/74 |
| 5,407,677 | 4/1995 | Tominaga et al. | 424/401 |
| 5,422,112 | 6/1995 | Williams | 424/401 |

*Primary Examiner*—Thurman K. Page
*Assistant Examiner*—Kathryne E. Shelborne
*Attorney, Agent, or Firm*—Charles J. Zeller

[57] ABSTRACT

A cosmetic mask product is disclosed comprising first and second compositions for sequential application to the face of a consumer, one of said composition containing an effervescent agent and the other of said composition containing an acid component.

39 Claims, No Drawings

FOAMABLE COSMETIC MASK PRODUCT

FIELD OF INVENTION

The present invention relates to cosmetic mask products for application to the surface of a consumer's skin, especially such products for application to the face of the consumer. More specifically, the present invention concerns a cosmetic mask product comprising a first composition containing an effervescent agent and a second composition containing an acid component, the first and second compositions being applied sequentially to cause a foaming action. Most specifically, the present invention concerns the treatment of skin, especially the face, comprising the sequential application of a cream mask as the first composition and a mask activator as the second composition, and optionally including the prior application of an efficacious skin treatment composition containing a high concentration of moisturizers and emollients.

BACKGROUND OF INVENTION

Skin treatment regimens are well known and typically consist of applying a lotion or cream product periodically to the skin of the consumer. U.S. Pat. Nos. 5,422,112 and 4,272,544 are illustrative of the prior art. The '544 patent discloses a cosmetic regimen consisting of the use of four components, namely, a cleanser, a cream, a lotion and a tonic. The prior art products of the lotion or cream type are generally massaged into the skin of the consumer. Accordingly they are not removed. Face masks are also available, generally referred to as "mud packs," that once applied to the surface of the skin harden to form a crustlike film, removable by soap and water.

SUMMARY OF INVENTION

The present invention concerns a cosmetic mask product for application to the skin of the consumer, in particular, to the face of the consumer. The cosmetic mask product comprises a first composition containing an effervescent agent in a cosmetically suitable vehicle and a second composition containing an acid component in a cosmetically suitable vehicle, the first and second compositions being sequentially applied to the skin of the consumer in any convenient order of application. Upon application of the last of the two compositions, a foaming action occurs as a result of gas being liberated by virtue of the reaction between the effervescent agent and the acid component, with concomitant release of heat of reaction. After a time the residue is removed from the skin of the user by means of a scraper or cloth.

The cosmetically suitable vehicle of one or both of the first or second compositions may contain one or more cosmetically useful adjuvants compatible with the cosmetic mask product, the adjuvants being selected from the group consisting of skin conditioning agents (including emollients, humectants and occlusive agents), abrasives, counterirritants including astringents, cleansing agents, biocides and anti-acne agents, each such adjuvant included in the first or second composition being present in an amount effective to provide its intended benefit when applied to the skin of the consumer. The cosmetically suitable vehicle of one or both of the first or second compositions also may contain one or more excipients compatible with the cosmetic mask product, the excipients being selected from the group consisting of emulsifying agents, foam boosters, emulsion stabilizers, hydrotropes, thickeners, binders, bulking agents, pH adjusting agents including buffers, chelating agents, preservatives, colorants and fragrance components.

The cosmetic mask product of the present invention comprising the first and second compositions contains sufficient water to permit the aqueous phase reaction of the effervescent agent with the acid component. Generally, each of the first and second compositions will contain water, although one of the compositions may be essentially anhydrous. The water content of the individual compositions is a function of the identity of the other constituents incorporated, as well as the requirement stated above that the combined first and second compositions provide sufficient water when applied to the skin to allow the aqueous phase reaction to take place in a cosmetically effective and safe manner.

Typically, one of the first or second compositions will further contain (i) about 0 to about 25% of a nonliquid organic material of moderate melting point, (ii) about 1 to about 20% of a surfactant system adapted to provide at least one of emulsification, cleansing and foam boosting, (iii) about 40 to about 90% water, and (iv) an amount of a thickening agent effective to provide a viscosity of from about 50,000 to about 1 million cps at 25° C. The other of the first or second compositions will typically contain (a) about 55 to about 90% of a cosmetically suitable organic solvent, (b) an amount of a thickening agent effective to provide a viscosity of from about 25,000 to about 500,000 cps at 25° C., and (c) about 0 to about 20% water as a cosolvent.

Generally, the effervescent agent will be included in the composition comprised of components (i) through (iv), while the acid component will be provided in the composition comprised of components (a) through (c). The first composition preferably containing the effervescent agent is preferably in the form of a lotion, cream or paste incorporating the aforementioned components (i) through (iv) and the second composition preferably containing the acid component is preferably in the form of a gel incorporating the aforementioned components (a) through (c). In a particularly preferred embodiment, the effervescent agent is sodium bicarbonate and the acid component is an α-hydroxy acid, in particular, lactic acid. The mixed composition is removed by cloth or other means, especially means to abrade the skin lightly to assist in removal of dirt, dead skin, oils and the like.

The cosmetic mask product is used by first applying a uniform layer of the first or second composition to the skin of the consumer using a spatula or other means. Thereafter, the other composition is applied to the skin of the consumer in any convenient way, and is massaged into the skin with consequential admixing. The mixed composition is maintained in contact with the skin for a predetermined period of time, but at least until a foaming action has occurred as a result of reaction between the effervescent agent (preferably contained in the first composition) and the acid component (preferably contained in the second composition).

In a preferred embodiment, the skin treatment system includes a pretreatment with an especially efficacious skin care composition, typically in the form of a lotion or cream, and containing a high level of skin moisturizers, humectants and emollients. This cream, hereinafter referred to as the "Moisturizing Cream," is applied to the skin as a uniform layer massaged gently into the skin, and kept in contact with the skin for a predetermined period of time. The cosmetic mask product of the present invention may be applied directly to the skin without removal of the Moisturizing Cream.

DETAILED DESCRIPTION OF THE INVENTION

The skin treatment system of the present invention comprises treatment of the skin with a foamable cosmetic mask product that comprises first and second compositions adapted for sequential application to the skin of the consumer, either of these compositions being suitable for first application to the skin of the consumer. One of the first or second compositions contains an effervescent agent and the other of these compositions contains an acid component. The skin treatment system may further comprise application of a Moisturizing Cream as a pretreatment composition, the Moisturizing Cream containing a high concentration of one or more of emollients, humectants, moisturizers, exfolients and essential oils.

The first composition is provided in the form of a composition that does not flow appreciably when applied to the skin, especially the face, of the consumer, and thus remains without dripping where applied. Compositions having a thixotropic theology are suitable. This first composition preferably contains the effervescent agent in a cosmetically suitable vehicle that includes one or more adjuvants and one or more excipients. Suitable adjuvants are skin conditioning agents such as emollients, humectants and occlusive agents; abrasives; counterirritants including astringents; cleansing agents; biocides; antimicrobials, and antiacne agents, each such adjuvant being present in said first composition in an amount effective to provide its intended benefit when applied to the skin of the consumer. Suitable excipients include emulsifying agents, foam boosters, emulsion stabilizers, hydrotropes, thickeners, binders, bulking agents, pH adjusting agents including buffers (other than the effervescent agent), chelating agents, colorants, preservatives and fragrance components. Other excipients might include gelling agents and organic solvents.

A suitable first composition is a cream comprising (i) about 0 to about 25% of a nonliquid organic material, (ii) about 1 to about 20% of a surfactant system adapted to provide at least one of emulsification, cleansing and foam boosting, (iii) about 40 to about 90% water, (iv) an amount of a thickening agent effective to provide a viscosity of from about 50,000 to about 1 million cps at 25° C., and (v) about 1 to about 20% of an effervescent agent. This first composition in cream form containing the effervescent agent is usually the first applied of the first and second compositions.

The second composition is also provided in the form of a composition that does not flow appreciably when applied to the skin, especially the face, of the consumer and is readily admixable with the first composition described above. The second composition preferably is in the form of a gel that contains the acid component in a cosmetically suitable vehicle that includes one or more excipients such as gelling agents, thickeners, organic solvents, chelating agents, pH adjusting agents including buffers (other than the acid component), colorants, preservatives and fragrances. Other excipients might include stabilizers and binders. Generally, the adjuvants are contained in the cream composition previously described, although adjuvants enumerated above in respect of the first composition to the extent compatible with the gel may be incorporated into the gel. Preferably, the gel will contain some water as a cosolvent along with an organic solvent, but may be anhydrous. This second composition in gel form containing the acid component is usually applied to the skin following application of the cream composition containing the effervescent agent.

A suitable second composition is a gel comprising (a) about 55 to about 90% of a cosmetically acceptable organic solvent suitable to permit gel formation; (b) an amount of a thickening agent effective to provide a viscosity of from about 25,000 to about 500,000 cps at 25°; (c) about 0 to about 20% water, and (d) about 1 to about 30% of an acid component.

These compositions and their use will be described in greater detail below. In the discussion that follows, the term "cream mask" (or "cream" if readily understood by context) will mean the first composition containing the components (i) through (iv) and the effervescent agent (v), while the term "gel activator" (or "gel" if readily understood by context) will mean the second composition containing the components (a) through (c) and the acid component (d). However, the practitioner of ordinary skill in the art will understand that such terms relate to the preferred forms of the first and second compositions, which have the more general definitions set forth above and in the Summary of Invention. For convenience the use of the cosmetic mask of the present invention will be described in connection with its application to the face of a consumer. However, the product is useful generally in the treatment of skin on the human body. All percentages unless otherwise indicated are percent by weight of the identified composition.

The Cream Mask Composition of the Cosmetic Mask Product

The cream mask is in the form of a cream having a viscosity of from 50,000 to 1 million, preferably from about 150,000 to about 500,000, most preferably from about 200,000 to about 400,000 cps at 25° C. The cream mask is applied to the skin uniformly as a relatively thin layer that remains in contact with the skin for a predetermined period of time prior to the application of the gel activator as described below.

The cream mask contains (i) about 0 to 25% of nonliquid organic material of moderate melting point, (ii) about 1 to 20% of a surfactant system adapted to provide one or more of emulsification, cleansing and foaming; (iii) about 40 to 90% water, (iv) an amount of a thickening agent effective to provide a viscosity in the aforementioned range, and (v) from about 1 to 20% of an effervescent agent.

The nonliquid organic material is incorporated to ensure that the cream composition has sufficient body, and thus will not drip or run when applied to the skin. The nonliquid organic material is selected preferably to further provide an emollient, humectant or other skin conditioning function when applied to the skin. It is incorporated in the cream composition in lieu of an oil emollient because oil emollients tend to suppress the foaming action obtained by the reaction of the effervescent agent and the acid component. Nonetheless, low levels of oil emollients, generally less than 1.0%, especially less than 0.2%, by total weight of the cosmetic mask product can be tolerated.

Preferably, the nonliquid organic material (i) is present in an amount of from about from about 1 to about 20%, and most preferably from about 5 to about 15% by weight of the cream composition. These materials are of a hydrophobic nature and are not readily soluble in water. The HLB of these materials is less than 10, especially less than about 6. These materials often have a waxy or waxlike consistency. The organic materials used in the cream composition of the present invention typically have a melting point above 125° F., preferably from about 125° to about 200° F., most preferably from about 135° to about 175° F. Materials identified in the CTFA Cosmetic Ingredient Handbook, pp. 79–84 (First Edition 1988) as skin conditioning agents are suitable provided they are nonliquid and hydrophobic, and especially if they have moderate melting points in the aforementioned preferred ranges. Useful materials are the saturated, primary fatty acids having from about 12 to about 22 carbons such as stearic, palmitic and behenic acids, and the fatty alkyl, glyceryl and lanolin esters of such acids;

saturated, primary fatty alcohols having from about 12 to about 22 carbons such as cetyl, stearyl and cetearyl alcohols; polyethylene glycols and the mono- and diesters thereof, and natural and synthetic waxes such as beeswax, microcrystalline wax, hydrogenated castor oil, paraffin wax and lanolin wax. These materials might have up to three, more typically two, mols ethylene oxide per molecule, provided they remain hydrophobic and nonliquid.

Although incorporation of the nonliquid organic material is highly preferred, it is regarded as an optional ingredient in the cosmetic mask product and for this reason is recited as being present in a 0% concentration. Thus, when the cosmetic mask product is used in a skin treatment system that pretreats the skin of the consumer with the Moisturizing Cream, the need to provide further emolliency via the cream mask is mitigated. Moreover, the benefits of the treatment received from the reaction of the effervescent agent and the acid component are not diminished. If necessary additional body can be provided by increasing the thickener concentration, although the organoleptics (feel, creaminess, etc.) of the cream mask may well suffer to some extent.

The cream mask contains from about 1 to 20% of a surfactant system that provides at least one of emulsification, cleansing, foam boosting or other function generally associated with a surfactant agent. As is well known in the cosmetic art, an individual surfactant may provide multiple functions in a cosmetic composition, and may act as a cleanser, an emulsifier and a foam booster in the cream mask composition of the present invention. However, a surfactant blend containing specific surfactants that excel in each function optimizes performance of the cosmetic mask product. The surfactant system may contain one surfactant, but typically will include a plurality of surfactants, to achieve the requisite function(s). Useful surfactants are identified in the CTFA Cosmetic Ingredient Handbook at pp. 87–97. Preferably, the surfactant system is present in an amount of from about 3 to about 15% by weight of the cream composition, most preferably in an amount of from 5 to 10%. The surfactants may be anionic, nonionic, cationic, amphoteric or zwitterionic, but often are nonionic to provide an emulsifying function and anionic or amphoteric to provide a cleansing function. Generally, the surfactants used in the surfactant system are at least water-dispersible and have an HLB of at least 10, often above about 12. Incompatible combinations (e.g., most anionic-cationic mixtures) should be avoided.

Representative nonionic surfactants useful in formulating the cream composition are disclosed in the CTFA Cosmetic Ingredient Handbook, pp. 90–97 (1st ed. 1988), which is incorporated herein by reference thereto, and include ethoxylated fatty alcohols preferably having 5 to 25 moles ethylene oxide; ethoxylated fatty acid esters preferably having about 5 to 50 moles ethylene oxide; ethoxylated glyceryl fatty acids preferably having about 12 to 30 moles of ethylene oxide; ethoxylated lanolin and ethoxylated lanolin acid esters preferably having about 5 to 75 moles ethylene oxide; ethoxylated alkylphenols especially having about 5 to 100 moles ethylene oxide; ethoxylated fatty esters and oils having preferably about 8 to 100 moles ethylene oxide; sorbitan esters and especially ethoxylated sorbitan esters preferably having about 8 to 75 moles ethylene oxide; polyoxyethylene/polyoxypropylene block copolymers, especially copolymers having the formula $(EO)_x(PO)_y(EO)_x$ wherein EO and PO represent ethylene oxide and propylene oxide units, respectively, and alkoxylated amines preferably having about 5 to 50 moles ethylene oxide. By the term "fatty" as used to describe acids, alcohols, amines and ethoxylated esters and oils useful as surfactants in the surfactant system is meant a substituent group or compound as the case may be having from about 10 to about 22, preferably 14 to 18, carbon atoms in the group or compound, which may be saturated or unsaturated. The degree of ethoxylation is selected to provide good emulsification properties.

Illustrative nonionic emulsifiers are identified below using the CTFA nomenclature, which is now in common use in the cosmetic/personal products industry and is employed routinely in ingredient labeling of such products*:
C11–15 Pareth-5, -7, -12, -20
Ceteareth-6, -8, -10, -15, -20, -55
Ceteth-6, -30
Isosteareth-10, -12, -20
Laneth-10, -15, -20
Laureth-7, -10, -12, -20, -25, -30
Nonoxynol-6, -10, -14
Octoxynol-7, -10, -16
PEG-5, -8 Cocoate
PEG-20, -150 Dioleate
PEG-20, -30 Glyceryl Stearate
PEG-25, -35, -50, -200 Hydrogenated Castor Oil
PEG-8, -10, -14 Laurate
PEG-10, 15, -40, -50, -100, -150 Stearate
Poloxamer 238, 288, 338
Poloxamine 904
PPG-27, -55 Glyceryl Ether
Steareth-7, -13, -16, -100

*In the above listing, several numbers follow the CTFA designation in certain instances, as in "Nonoxynol-6, -10 . . ." or "Poloxamer 238, 288 . . ." to indicate several compounds, i.e., Nonoxynol-6, Nonoxynol-10, Poloxamer 238, Poloxamer 288, etc.

Preferred are glyceryl esters and polyethoxylated esters of fatty acids and ethoxylated fatty alcohols, all having at least 5 mols EO. Highly ethoxylated hydrogenated oils are also preferred.

Representative anionic surfactants useful in formulating the cream composition are disclosed in the CTFA Handbook at pp. 87–90, which is incorporated herein by reference thereto, and include ammonium, sodium and potassium salts of: fatty acids, fatty acid amides of N-methyl taurine, fatty acid esters of taurines, fatty acid esters of isethionic acid, alkyl sulfates, fatty acid amides of glutamic acid, fatty acyl derivatives of sarcosines, e.g., sodium myristoyl sarcosinate, and the ethoxylated derivatives of the foregoing. The preferred anionic surfactants would be mild to the skin, and such surfactants include the taurates, sarcosinates and the isethionates. The fatty alkyl moiety is as described with regard to the nonionic surfactants.

Illustrative cleansing anionic surfactants are listed below (as the sodium salt):*
Sodium Cetyl Sulfate
Sodium Cetearyl Sulfate
Sodium Cocoate
Sodium Cocoyl Isethionate
Sodium Cocoyl Sarcosinate
Sodium Laurate
Sodium Laureth Sulfate
Sodium Laureth -5, -7, -12 Sulfate
Sodium Lauroyl Sarcosinate
Sodium Lauroyl Taurate
Sodium Lauryl Sulfate
Sodium Methyl Cocoyl Taurate
Sodium Methyl Oleoyl Taurate
Sodium Nonoxynol -1, -4 Sulfate
*See footnote at page 13.

Amphoteric surfactants also have good cleansing properties and advantageously are nonirritating. Suitable amphoteric surfactants are betaines such as coco-betaine, cocamidopropyl betaine, cocoamidopropyl hydroxysultaine, and the like. It is understood, however, that nonionic surfactants also have cleansing properties and may be substituted for the anionic or amphoteric surfactant.

The thickening agent is one typically used in aqueous compositions, and includes gums, resins, minerals and organic salts. The thickening agent is present in an amount to stably thicken the composition to a viscosity of from about 50,000 to about 1 million cps at 25° C., preferably 150,000 to 500,000, especially from about 200,000 to 400,000 cps at 25° C. Thickening agents include cellulose and its derivatives, especially carboxymethyl hydroxyethyl cellulose, hydroxy ethyl ethylcellulose, hydroxypropyl methylcellulose and methyl cellulose; carbohydrates such as carrageenan, alginate, agar, guar gum and its derivatives, starch and modified starch, β-glucans, and xanthan gum; magnesium aluminum silicate; clays such as attapulgite, bentonite, montmorillonite and hectorite; acrylics; acrylate resins, e.g., carbomers, and certain polymers and copolymers, e.g., polyvinyl alcohol. Generally the thickening agent is present in an amount of from 0.1 to about 5% by weight of the cream composition, preferably from about 0.1 to about 3%, most preferably from about 0.5 to about 2%. Especially preferred are bentonite, magnesium aluminum silicate, xanthan, and β-glucan. Some viscosity changes with time may occur. The values recited are for the product as received by the consumer, i.e., following warehousing for one or more months. The cream mask should not be so thick as to make it difficult to apply or to prevent the reaction between the effervescent agent and the acid component from taking place.

The effervescent agent will release a gas upon reaction with the acid component. The amount of the effervescent agent present in the composition will be such as to generate a sufficient amount of gas to obtain a foaming action. The reaction between the effervescent agent and the acid component is exothermic and imparts an organoleptically noticeable warming of the surface of the skin of the consumer. Suitable effervescent agents are the ammonium, sodium and potassium salts of bicarbonate and carbonate. The effervescent agent is generally present in the cream composition in an amount of from about 1 to about 20%, preferably about 3 to about 15%, most preferably from about 3 to about 10% by weight.

Water is present in the cream mask in an amount of from about 40 to about 90%, preferably from about 60 to about 80%. The cream mask is the preferred primary repository for the water of the cosmetic mask product needed as the reaction medium for the reaction between the effervescent agent and the acid component. Because a portion of the water can be provided in the gel activator, however, the formulator enjoys wide latitude in the amount of water incorporated into the cream mask, and may select such amount, in concert with the amount of water contained in the gel activator, to enhance organoleptic properties of the cream mask, to enhance its physical properties, or to facilitate manufacture.

The pH of the cream composition is alkaline, generally from above 7.5 to about 9, preferably from about 7.8 to 8.5, in particular between 7.8 to 8.3. If the pH is too low, the cream mask will evolve gas by decomposition of the effervescent agent. Above about 9 the cream mask tends to be irritating to the skin. The pH may be adjusted if necessary using a pH adjusting agent such as sodium hydroxide or other alkali materials such as alkanolamines, etc.

The cream composition optionally contains from about 0.001 to about 0.25%, preferably from about 0.05 to about 0.1% by weight of a counterirritant which includes essential oils and certain astringents. The essential oil is present in such low amount that it does not appreciably affect foaming of the composition upon admixing of the cream and get compositions. The essential oil acts as a counterirritant that dilates the capillary blood vessels proximate the surface of the skin, producing a cooling effect in advance of the heating effect provided by reaction of the effervescent agent and the acid component. Suitable essential oils are sandalwood, eucalyptus, peppermint, menthol, spearmint, rose and clove. The essential oils also impart a pleasing scent to the cream product. Also useful for this function is witch hazel, an astringent.

The cream composition may contain other optional adjuvants to provide a cosmetic benefit. Illustrative of such adjuvants are skin conditioning agents that are oils at room temperature, provided they are present in the cosmetic mask product at a total concentration of less than 1% by weight, preferably less than 0.2% by weight. Such skin conditioning agents include, e.g., isopropyl myristate, isopropyl palmitate isodecyl neopentanoate, squalene, mineral oil, $C_{12-15}$ benzoate and hydrogenated polyisobutene. The cream composition may contain a gentle abrasive material such as almond meal, oatmeal, wheat flour, pumice, diatomaceous earth, polyethylene and the like, to assist in the removal of skin surface cells. The abrasive is typically present in an amount of less than 5%, typically between about 1 to 5%. Yet another optional adjuvant is a biocidal or antimicrobial material having cosmetic utility such as triclosan, cetylpyridium chloride and benzalkonium chloride, which are present typically in an amount of less than about 0.5% by weight of the cream mask, preferably less than about 0.1% by weight. Salicylic acid is a known antiacne agent, but would not be incorporated into the cream mask containing the effervescent agent.

Suitable optional components having excipient benefits that may be incorporated into the cream mask are preservatives such as methyl paraben, propyl paraben, and imidiazolidinyl urea and the like, and antioxidants such as BHA, BHT, sodium ascorbate, sodium citrate, tocopherol acetate and sodium sulfite. Preservatives and antioxidants are each generally present in an amount of less than 1%, especially less than about 0.1%. The cream composition preferably contains a chelating agent, for example, trisodium EDTA, which is generally present in an amount of less than about 1%, especially less than about 0.5%. A colorant, i.e., a dye, pigment or pearlizing agent, can be employed in an amount of less than about 1% to provide a pleasing color or visual effect to the cream product. FD&C dyes are preferred.

The Gel Activator Composition of the Cosmetic Mask Product

The gel activator composition is provided as a carrier for the acid component, and as such typically does not contain cosmetic active components. Advantageously, the preferred gel form of the activator composition is manufactured using conventional technology, is stable at acid pH and is easily applied to the face of the consumer from a tube or other user-friendly container. The gel activator comprises, in addition to the acid component, (a) about 55 to 90% of an organic solvent, (b) about 0 to about 20% water, (c) an amount of a thickening agent to provide a viscosity of from about 25,000 to about 500,000 cps at 25° C., and (d) an amount of a buffering agent, including zero, effective to provide a pH of from about 3.5 to about 6.

Any cosmetically acceptable acid can be employed as the acid component, although inorganic acids are not preferred as they can be irritating if not used carefully. The acid component is present in the gel composition in an amount of from 1 to about 30%, preferably in an amount of from about 5 to about 15% by weight of the composition. Of the inorganic acids, hydrochloric acid and phosphoric acid of dilute concentration are especially suitable. Preferably, an organic acid will be employed, in particular, an organic acid such as ascorbic acid having a pKa of from about 1 to about 9, especially 2 to about 5. The α-hydroxy acids are preferred as they are mild, yet can provide an exfoliating effect on the skin. Of the α-hydroxy acids, mention may be made of lactic, glycolic, citric, malic, tartaric, mandelic and benzilic acids. β-hydroxy acids are also useful, especially salicyclic acid, which also can provide an antiacne benefit. Lactic acid is especially preferred.

The organic solvent component is a material suitable for use in cosmetic compositions, especially gels. The solvent is typically a mono- or dihydric alcohol having from 3 to about 8 carbons. Such compounds include isopropyl alcohol, n-butyl alcohol, hexanol, propylene glycol, butylene glycol, ethyl hexanediol and dipropylene glycol. Also suitable are low molecular weight polyethylene glycols, polyalkene glycols, mannitol, sorbitol and water-soluble esters. The organic solvent is present in an amount of from about 55 to about 90%, preferably about 70 to about 85%, by weight of the activator composition. Butylene glycol is preferred.

Water is a cosolvent along with the organic solvent and is present in an amount of from about 0 to about 20% by weight of the gel composition, preferably from about 5 to about 15% by weight of the gel composition. The amount of water may be adjusted in concert with the water content of the cream mask to provide the requisite amount of water in the cosmetic mask product. Thus, wide latitude exists in the amount of water incorporated and may be adjusted to provide particular physical properties to the gel or to facilitate manufacture. Water present in the gel composition will assist in hydration of the gel matrix.

Suitable thickening agents are those previously identified in respect of the cream composition, especially the natural resins such as the cellulose derivatives and the gums such as xanthan and carragennan. Hydroxyethyl ethylcellulose is especially suitable to produce a clear thixotropic gel of low pH. The thickening agent is typically present in an amount of from about 0.1 to about 3%, preferably from about 0.5 to about 1.5%, to provide the desired viscosity previously disclosed. The preferred viscosity is generally from about 50,000 to about 250,000, and especially from about 50,000 to about 175,000 cps at 25° C.

It has been found that activation of the reaction in terms of the effervescent effect is superior when the acid component is present in a gel composition. Accordingly, in the preferred embodiment the activator composition is in the form of a gel that has a low water content but a high organic solvent concentration. Conversely, the cream composition is a highly aqueous system that provides the requisite water for the aqueous phase effervescent agent-acid component reaction to take place.

The gel activator composition generally contains a pH adjusting agent to provide and to maintain the pH at the desired level. The pH adjusting agent in the gel activator composition provides a pH of from about 3.5 to about 6, preferably from 4 to 5, and is present in a concentration as required to provide such pH. Suitable pH adjusting of agents are ammonium hydroxide, sodium hydroxide, potassium, hydroxide, mono-, di- and triethanolamine and aminomethylpropanol.

Optional materials useful for incorporation in the accelerator composition include those optional components identified above in respect of the cream composition.

Moisturizing Cream Pretreatment Composition

Optionally, the skin conditioning regimen may include application of product rich in moisturizers, emollients, humectants and the like in advance of the application of the cosmetic mask product of the present invention. This composition is applied to the skin, especially to the face of the consumer, and gently massaged into the skin, and left in contact with the skin for a predetermined period of time. The product is applied to the face for up to 30 minutes, preferably for up to 15 minutes, following which the cosmetic mask product of the present invention is applied. Lower contact times between 2 to 15 minutes are employed in the case of Moisturizing Creams containing an exfoliant. The pretreatment skin treatment product is not removed from the skin. While the pretreatment moisturizing cream may be a conventional product, for example, Firm Defense Cream® manufactured by Matrix Essentials, Inc., it is preferably formulated to provide a gentle exfoliation of the skin, which loosens dirt, and enhances the action of the foam produced by reaction of the effervescent agent and the acid component of the cosmetic mask product. Useful exfoliants are α-hydroxy acids and β-hydroxy acids, which are present in the Moisturizing Cream pretreatment composition in an amount up to about 30%, preferably from about 1 to about 20%, most preferably in an amount of about 5 to about 15% by weight of the Moisturizing Cream pretreatment composition. When such acids are used, the composition is buffered, e.g., using ammonium or sodium hydroxide, to a pH of from about 3.5 to about 6, preferably from about 4 to about 5.

Because the Moisturizing Cream is substantially completely absorbed into the skin before application of the cream composition of the cosmetic mask product, it may contain emollient oils such as dimethicone, isopropyl myristate, isopropyl sebacate, isopropyl palmitate, mineral oil and hydrogenated polyisobutene, as well as other skin care constituents previously identified herein. A skin care product sold commercially especially useful as the Moisturizing Cream pretreatment composition is Age Recovery Alpha Renewal® Treatment Cream sold by Matrix Essentials, Inc. Also suitable is Lac-Hydrin® 5% and Lac-Hydrin® 12% sold by Westwood Squibb, Inc.

Use of the Cosmetic Mask Product

The composition of the cosmetic mask product containing the effervescent agent is generally applied first, followed by application of the composition containing the acid component. However, this order of application may be reversed if longer contact between the acid component and the skin is desired to enhance exfoliation of the skin, especially in the absence of pretreatment with a Moisturizing Cream that contained an exfolliant.

The first composition, usually the cream mask composition containing the effervescent agent, is applied uniformly over the area of treatment, e.g., in the case of a facial treatment, the cream is applied to forehead, cheeks, around the eyes, chin, etc., in a thin film about 0.5 to 5 mm thick or about 5 to about 30 g of cream composition in most instances. In general, the cream mask composition is allowed to remain on the face in contact with skin for up to about 10 minutes. Preferably, however, the second composition that is the acid component-containing gel activator is applied shortly after application of the first composition, i.e., from several seconds to about five minutes, usually less than about one minute following application of the first composition.

The gel activator composition is applied such that the acid component is generally substantially completely depleted by reaction with the effervescent agent. The metering of the gel activator is easily accomplished by applying the gel from a tube as a bead of predetermined diameter with instructions identifying where the bead is to be applied to the face of the consumer. Of course the user, especially the salon professional, may be instructed to measure the quantity of the first and second composition by weight or volume. For the retail market, premeasured packets may be provided.

Generally, from about 5 to about 30 g of the gel activator containing the acid component are applied to the face of the consumer in a bead from 1/16 to 1/8 inch in diameter. The cream-to-gel weight ratio is typically from about 1:2 to about 4:1, preferably from about 1:1 to about 3:1, and most preferably about 2:1. The gel may be applied in two or more doses up to about 15 minutes, generally less than about 5 minutes, apart. The gel bead is then admixed into the cream composition using a spatula or other means, with commencement of reaction accompanied by heat and foaming. The foaming occurs because released gas, i.e., carbon dioxide when the effervescent agent is sodium bicarbonate, is percolating through the relatively viscous cream-gel admixture. Although the cosmetic mask product contains surfactants that can enhance the foaming effect, the foaming does not occur in the absence of the reaction.

The total amount of gel composition applied to the face is usually such that essentially complete reaction of the acid component with the effervescent agent takes place. That is, the amount of effervescent agent applied to the face of the consumer is generally in a stoichiometric excess over the amount of the acid component applied to the face of the consumer. This ensures that the foaming cosmetic mask product composition on the surface of the skin obtained by admixing the cream and gel compositions will have a neutral to somewhat alkaline pH. Typically, then, the mole ratio of the effervescent agent to the acid component as applied to the face of the consumer is from 1:1 to about 4:1, preferably about 1.5:1 to about 3:1. Because the cream and the gel are both viscous compositions, the time for complete reaction is delayed somewhat, permitting contact of the skin with the acid component. In some instances, however, it may be desirable to maintain an acidic composition on the face of the consumer following complete reaction, and in such cases the acid component may be maintained in a stoichiometric excess over the amount of the effervescent agent, as such constituents are applied to the face of the consumer. This instance may arise when the initial concentration of the acid component in the gel activator is in excess of 20% by weight, and gentle "peel" of the skin is desired. Usually, no pretreatment with an exfoliating Moisturizing Cream occurs in such case.

As previously explained, the effervescent agent is generally in a stoichiometric excess over the amount of the acid component in the cosmetic mask product, thereby ensuring essentially complete reaction of the acid component. Coupled with suitably written instructions, this excess also lessens the degree of accuracy needed in metering the relative amounts of the cream and gel compositions. The cosmetic mask product requires sufficient water to ensure nonirritating reaction of the effervescent agent and the acid component on the skin of the consumer. Generally, the amount of water depends on the amount and solubility of the reactants, and thus it is especially preferred to selected reactants that are fairly soluble, such as sodium bicarbonate and lactic acid. Suitable solubility in water is above 1 g/100 cc.

The combined first and second compositions comprising the cosmetic mask product are maintained in contact with the skin for up to about 30 minutes, preferably for about 5 to 15 minutes. Thereafter the residue is removed by means of a cloth or scraper as is known in the art. The face of the consumer may then be washed with a gentle soap composition.

The regimen comprising application of the Moisturizing Cream product, application of the first composition containing one of the effervescent agent or the acid component, and application of the second composition containing the other of the effervescent agent or the acid component improves skin tone, texture and softness, and removes dead cells that cling to the surface of the skin and thus accentuate discontinuities in the surface of the skin. Additionally, the skin treatment regimen may alleviate localized skin inflammations caused by bacteria.

Manufacture

The cosmetic mask product is manufactured using conventional methods used in the manufacture of like products. Thus, the hydrophobic and hydrophilic constituents of these compositions are typically combined at elevated temperatures to form premixes, and then blended together to form the final product. In the case of the effervescent agent-containing product, it is preferred to incorporate the effervescent agent as the last component and into a composition having a pH sufficiently high to avoid gas formation. An alkalizing agent such as sodium hydroxide may be incorporated for this purpose.

In the case of the gel activator composition, all ingredients may be combined in a single batch, typically sequentially, with good mixing and at elevated temperature to assist in dissolution. A premix of the thickener and of the dye with deposits of the solvent may be useful to facilitate mixing and gelation. Following gel formation, the batch is cooled.

The present invention is further illustrated by the Examples below.

EXAMPLE 1

|  | Wt. % |
|---|---|
| Cream Composition | |
| Water | Q.S. 100% |
| Sodium bicarbonate | 5.0 |
| Sodium methyl cocoyl taurate | 5.0 |
| Cetearyl alcohol | 3.5 |
| Glyceryl stearate | 1.5 |
| Cetyl alcohol | 5.0 |
| PEG-100 stearate | 1.5 |
| PEG-40 castor oil | 1.5 |
| Essential oil | 0.01 |
| Preservative | 1.0 |
| Colorant | 0.4 |
| Xanthan gum | 1.5 |
| Trisodium EDTA | 0.2 |
|  | 100.00 |

Viscosity = 302,000 cps at 25° C.
pH = 8.0

| Gel Activator | |
|---|---|
| Water | Q.S. 100% |
| Butylene glycol | 78.0 |
| Hydroxyethyl ethylcellulose | 1.0 |
| Sodium hydroxide (50%) | 2.0 |
| Lactic acid (88%) | 9.1 |
|  | 100.0 |

Viscosity = 53,000 cps at 25° C.
pH = 4.9

The cream is applied to the face of the consumer uniformly and without massaging into the skin. The gel activator composition is then applied in the form of a bead approximately ⅛ inch in diameter over the cream composition and to the forehead, cheeks and chin, and is then admixed into the cream by gentle massage or by means of a spatula. The combined compositions begin to foam in light of the reaction between the bicarbonate and the lactic acid. The foaming is not due to the presence of the surfactants in the cream composition, but rather to the bubbling of carbon dioxide through the mixed composition. Of course the formation of a good foam in an aqueous system will be enhanced by the inclusion of a surfactant. The consumer experiences a cooling sensation of the skin upon application of the cream composition, which is then followed by a warming of the skin attributable to the exothermic heat of reaction. In this example approximately 16 g of the cream were applied to the face of the consumer, and approximately 8 g of the gel were applied. After about 10 minutes, the cosmetic mask is removed from the face of the consumer using a scraper and the face is then washed.

EXAMPLE 2

The same as Example 1 but application of the cosmetic mask is preceded by application of 8 g of the gel activator. The cosmetic mask is applied 5 minutes later.

EXAMPLE 3

The same as Example 1 or Example 2, but the cosmetic mask is preceded by application of LacHydrin® 5% as the Moisturizing Cream.

EXAMPLE 4

The same as Example 1, except the sodium bicarbonate component is contained in the gel accelerator at a 5% level. The lactic acid (88%) and the sodium hydroxide (50%) components of Example 1 are contained in the cream composition at 8% and 2% levels, respectively. The cream composition containing the lactic acid and sodium hydroxide components is applied first, but in an amount of 9 g. Approximately 15 g of the gel composition containing the sodium bicarbonate is applied to the face of the consumer.

I claim:

1. A cosmetic mask product for treating the skin of a consumer comprising a first composition and a second composition, one of said first and second compositions containing from about 1 to about 20% of an effervescent agent and the other of the compositions containing from about 1 to about 30% of an acid component, said compositions being adapted for sequential application to the skin of the consumer and in consequence thereof each of said compositions further comprising a cosmetically suitable vehicle, at least one of said first and second compositions containing as part of said vehicle at least one cosmetic adjuvant selected from the group consisting of nonliquid organic materials providing a skin conditioning benefit, abrasives, counterirritants, surfactants as cleansing agents, biocides, and antiacne agents that is compatible with the cosmetic mask product and with the composition in which it is contained, the at least one adjuvant being present in an amount effective to provide its intended function, and the cosmetic mask product incorporating an amount of water in the first and/or second compositions effective as a medium for the reaction of the effervescent agent and the acid component when the first and second compositions are sequentially combined on the skin of the consumer.

2. The cosmetic mask product of claim 1 wherein the first composition is in the form of a cream and contains the effervescent agent, and wherein the second composition is in the form of a gel and contains the acid component.

3. The cosmetic mask product of claim 1 wherein for each of the first and the second compositions the cosmetically suitable vehicle contains one or more excipients selected from the group consisting of thickeners, binders, suspending aids, chelating agents, gelling agents, pH adjusting agents, and, together with a surfactant cleansing agent as may be present in said first or second composition, a surfactant system comprising at least one surfactant to provide an emulsifying or foam boosting benefit, the excipient being present in the first and the second compositions in an amount effective to provide its intended function.

4. A cosmetic mask product comprising a first composition containing 1 to 20% of an effervescent agent and a second composition containing 1 to 30% of a cosmetically acceptable acid component, one of said first and second compositions further comprising (i) about 0 to 25% of a nonliquid hydrophobic organic material having skin conditioning efficacy; (ii) about 1 to 20% of a surfactant system adapted to provide one or more of emulsification, cleansing and foaming; (iii) about 40 to 90% water, and (iv) an amount of a thickening agent effective to provide a viscosity of from about 50,000 to 1 million cps at 25° C., and the other of said first and second compositions further comprising (a) about 55 to 90% of a cosmetically suitable organic solvent; (b) about 0 to 20% water, and (c) an amount of a thickening agent effective to provide a viscosity of from about 25,000 to 500,000 cps at 25° C., the amount of water present in the cosmetic mask product being sufficient to provide an aqueous medium for the reaction of the effervescent agent and the acid component when the first and second compositions are combined on the skin of the consumer.

5. The product of claim 4 wherein the first composition contains components (i) through (iv) and wherein the second composition contains components (a) through (c).

6. The product of claim 5 wherein the first composition is a cream and wherein the second composition is a gel.

7. The product of claim 4 or 6 wherein the nonliquid organic material is selected from the group consisting of fatty acids and the fatty alkyl and glyceryl esters of such acids; fatty alcohols; polyethylene glycols and the mono- and diesters thereof, and waxes.

8. The product of claim 4 or 6 wherein the surfactant system comprises at least one nonionic emulsifying surfactant.

9. The product of claim 8 wherein the nonionic surfactant is selected from the group consisting of ethoxylated fatty alcohols; ethoxylated fatty acids; ethoxylated glyceryl fatty acids esters; ethoxylated lanolin and ethoxylated lanolin acid esters; ethoxylated alkylphenols; ethoxylated fatty esters and oils; ethoxylated sorbitan and ethoxylated sorbitan esters; polyoxyethylene/polyoxypropylene block copolymers, said nonionic surfactants having an HLB of at least 10.

10. The cosmetic mask product of claim 8 wherein the surfactant system further comprises an anionic or amphoteric cleansing surfactant.

11. The cosmetic mask product of claim 10 wherein the anionic or amphoteric cleansing surfactant is selected from the group consisting of ammonium, sodium and potassium salts of fatty acids, fatty acid esters of taurines, fatty acid esters of isethionic acid, alkyl sulfates, fatty acyl derivatives of sarcosines, and the ethoxylated derivatives of the foregoing; betaines and sultaines.

12. The cosmetic mask product of claim 1, 4 or 6 wherein the effervescent agent is selected from the group consisting of ammonium, sodium and potassium carbonates and bicarbonates, and is present in said first or second composition in an amount of from about 3 to about 15%.

13. The cosmetic mask product of claim 12 wherein the acid is an organic acid having a p$K_a$ of from about 1 to about 9, and is present in said first or second composition in an amount of from about 5 to about 15%.

14. The cosmetic mask product of claim 13 wherein the acid component is selected from the group consisting of α-hydroxy, β-hydroxy acids and mixtures thereof.

15. The cosmetic mask product of claim 14 wherein the acid component is selected from the group consisting of lactic acid, glycolic acid, malic acid, tartaric acid, citric acid and mandelic acid.

16. The cosmetic mask product of claim 6 wherein the thickener for each of the first and second compositions is selected from the group consisting of cellulosic materials, carbohydrates and clays, and provides a viscosity of the first composition of from about 150,000 to about 500,000 cps at 25° C., and of the second composition of from about 25,000 to about 250,000 cps at 25° C.

17. The cosmetic mask product of claim 13 wherein the first composition comprises from about 0.001 to about 0.1 of a counterirritant.

18. The cosmetic mask product of claim 13 wherein the nonliquid organic material is present in an amount of from about 1 to about 20% by weight of the first composition.

19. The cosmetic mask product of claim 1 or 4 comprising 1 to 4 parts by weight of the effervescent-containing composition per part of the acid component-containing composition.

20. A method of treating skin cosmetically comprising the steps of applying sequentially to the skin a first composition and a second composition, one of said first and second compositions containing from about 1 to about 15% of an effervescent agent and the other of the compositions containing from about 1 to about 30% of an acid component, each of said compositions further comprising a cosmetically suitable vehicle, at least one of said first and second compositions containing as part of said vehicle at least one cosmetic adjuvant selected from the group consisting of nonliquid organic materials providing a skin conditioning benefit, abrasives, biocides, counterirritants, surfactants as cleansing agents and antiacne agents that are compatible with the sequential cosmetic treatment with the first and second compositions, the at least one adjuvant being present in an amount effective to provide its intended function, and the first and/or second composition containing in combination an amount of water effective as a medium for the reaction of the effervescent agent and the acid component when the first and second compositions are sequentially combined on the skin of the consumer.

21. The method product of claim 20 wherein the first composition is in the form of a cream and contains the effervescent agent, and wherein the second composition is in the form of a gel and contains the acid component.

22. The method of claim 21 wherein for each of the first and the second compositions the cosmetically suitable vehicle contains one or more excipients selected from the group consisting of thickeners, binders, suspending aids, chelating agents, gelling gents, pH adjusting agents, and together with a surfactant cleansing agent as may be present in said first or second composition, a surfactant system comprising at least one surfactant to provide an emulsifying or foam boosting benefit, the excipient being present in the first and the second compositions in an amount effective to provide its intended function.

23. A method of treating skin comprising the steps of applying sequentially to the skin a first composition containing 1 to 20% of an effervescent agent and a second composition containing 1 to 30% of a cosmetically acceptable acid component, one of said first and second compositions further comprising (i) about 0 to 25% of a nonliquid organic material having skin conditioning efficacy; (ii) about 1 to 20% of a surfactant system adapted to provide one or more of emulsification, cleansing and foaming; (iii) about 40 to 90% water, and (iv) an amount of a thickening agent effective to provide a viscosity of from about 50,000 to 1 million cps at 25° C., and the other of said first and second compositions further comprising (a) about 55 to 90% of a cosmetically suitable organic solvent; (b) about 0 to 20% water, and (c) an amount of a thickening agent effective to provide a viscosity of from about 25,000 to 500,000 cps at 25° C., the total amount of water present in the first and second compositions being sufficient to provide a medium for the reaction of the effervescent agent and the acid component when the first and second compositions are combined on the skin of the consumer.

24. The method of claim 23 wherein the first composition contains components (i) through (iv) and wherein the second composition contains components (a) through (c).

25. The method of claim 24 wherein the first composition is a cream that is first applied to the skin and wherein the second composition is a gel.

26. The method of claim 20 or 24 wherein the nonliquid organic material is selected from the group consisting of fatty acids and the fatty alkyl and glyceryl esters of such acids; fatty alcohols; polyethylene glycols and the mono- and diesters thereof, and waxes.

27. The method of claim 23 or 25 wherein the surfactant system comprises at least one nonionic emulsifying surfactant.

28. The method of claim 27 wherein the nonionic surfactant is selected from the group consisting of ethoxylated fatty alcohols; ethoxylated fatty acids; ethoxylated glyceryl fatty acid esters; ethoxylated lanolin and ethoxylated lanolin acid esters; ethoxylated alkylphenols; ethoxylated fatty esters and oils; ethoxylated sorbitan and ethoxylated sorbitan esters; polyoxyethylene/polyoxypropylene block copolymers, said nonionic surfactants having an HLB of at least 10.

29. The method of claim 27 wherein the surfactant system further comprises an anionic or amphoteric cleansing surfactant.

30. The method of claim 29 wherein the anionic or amphoteric cleansing surfactant is selected from the group consisting of ammonium, sodium and potassium salts of fatty acids, fatty acid esters of taurines, fatty acid esters of isethionic acid, alkyl sulfates, fatty acyl derivatives of sarcosines, and the ethoxylated derivatives of the foregoing; betaines and sultaines.

31. The method of claim 20, 23 or 25 wherein the effervescent agent is selected from the group consisting of ammonium, sodium and potassium carbonates and bicarbonates, and is present in said first or second composition in an amount of from about 3 to about 15%.

32. The method of claim 31 wherein the acid is an organic acid having a p$K_a$ from about 1 to about 9, and is present in said first or second composition an amount of from about 5 to about 15%.

33. The method of claim 32 wherein the acid component is selected from the group consisting of α-hydroxy, β-hydroxy acids and mixtures thereof.

34. The method of claim 33 wherein the acid component is selected from the group consisting of lactic acid, glycolic acid, malic acid, citric acid, tartaric acid and mandelic acid.

35. The method of claim 25 wherein the thickener for each of the first and second compositions is selected from the group consisting of cellulosic materials, carbohydrates and clays, and provides a viscosity of the first composition of from about 150,000 to about 500,000 cps at 25° C., and of the second composition of from about 25,000 to about 250,000 cps at 25° C.

36. The method of claim 32 wherein the first composition comprises from about 0.001 to about 0.1 of a counterirritant.

37. The method of claim 32 wherein the nonliquid organic material is present in an amount of from about 1 to about 20% by weight of the first composition.

38. The method of claim 20 or 23 wherein 1 to 4 parts by weight of the effervescent-containing composition is applied to the skin per part of the acid component-containing composition.

39. The method of claim 20 or 23 further comprising applying a moisturizing cream in advance of the application of the first and second compositions.

* * * * *